United States Patent [19]

Vergara et al.

[11] Patent Number: 5,178,861
[45] Date of Patent: * Jan. 12, 1993

[54] CROSS-REACTIVE AND PROTECTIVE EPITOPES OF CIRCUMSPOROZOITE PROTEINS

[75] Inventors: Ulises Vergara, Brooklyn; Andres Ruiz, Queens; Arturo Ferreira, New York; Ruth S. Nussenzweig, New York; Victor N. Nussenzweig, New York, all of N.Y.

[73] Assignee: New York University, New York, N.Y.

[*] Notice: The portion of the term of this patent subsequent to Apr. 10, 2007 has been disclaimed.

[21] Appl. No.: 370,241

[22] Filed: Jun. 22, 1989

Related U.S. Application Data

[63] Continuation of Ser. No. 115,634, Oct. 26, 1987, Pat. No. 4,915,942, which is a continuation of Ser. No. 649,903, Sep. 12, 1984.

[51] Int. Cl.⁵ .................... H61K 35/74; H61K 37/02; C07K 7/00

[52] U.S. Cl. ..................................... 424/88; 530/327; 530/326; 530/325; 514/12; 514/13

[58] Field of Search ....................... 530/326, 327, 325; 424/88; 514/12, 13

[56] References Cited

U.S. PATENT DOCUMENTS

| | | | |
|---|---|---|---|
| 4,466,917 | 8/1984 | Nussenzweig et al. | 530/350 |
| 4,769,235 | 9/1988 | Schlesinger et al. | 424/88 |
| 4,915,942 | 4/1990 | Vergara et al. | 424/88 |

Primary Examiner—Merrell C. Cashion, Jr.
Assistant Examiner—S. G. Marshall
Attorney, Agent, or Firm—Darby & Darby

[57] ABSTRACT

Disclosed is a peptide antigen comprising an amino acid sequence of a non-repetitive epitope of the circumsporozoite protein of a sporozoite of the genus plasmodium said peptide having the property of eliciting formation of antibodies that bind to said nonrepetitive epitope on the sporozoite surface said peptide being synthetic, purified and substantially shorter in length than said protein.

2 Claims, 3 Drawing Sheets

CROSS-REACTIVE AND PROTECTIVE EPITOPES OF CIRCUMSPOROZOITE PROTEINS

The government has rights to this invention based on research support in the form of Grant No. AID-DPE-0453-C-00-2002-00 from the Department of State, Agency for International Development.

This is a continuation of application Ser. No. 115,634, filed Oct. 26, 1987, now U.S. Pat. No. 4,915,942 which in turn is a continuation of application Ser. No. 649,903, filed Sep. 12, 1984.

BACKGROUND OF THE INVENTION

The present invention relates to polypeptide antigens suitable for providing protective immunity against malaria by incorporation into a vaccine. These antigens have amino acid sequences corresponding to segments of the amino acid sequence of the circumsporozoite protein that lie outside the bounds of the tandemly repeated domain of such protein. The antigens of the present invention can be used to elicit formation of antibodies, which recognize sporozoites not only of the same species of plasmodium from which these antigens were derived, but of other species as well.

The present application incorporates by reference the entire disclosures of:

(a) U.S. Pat. No. 4,466,917 of Nussenzweig, R., et al., issued on Aug. 21, 1984;

(b) assignee's copending U.S. patent application Ser. No. 574,553 of Ellis, J. et al., filed on Jan. 27, 1984 and entitled Protective Peptide Antigen; and (c) assignee's copending U.S. patent application Ser. No. 633,147 of Ellis, J. et al., filed on Jul. 23, 1984 and entitled Protective Peptide Antigen Corresponding to Plasmodium Falciparum Circumsporozoite Protein. Pertinent excerpts of the disclosures of these applications have been published in U.S. Pat. No. 4,915,942 of which the present is a continuation.

In most instances, malaria infections are initiated by the introduction of sporozoites (highly immunogenic forms of the malaria parasite) into the bloodstream of a host through the bite of an infected mosquito. The immunogenicity of sporozoites resides largely, if not exclusively, in a single antigen, the circumsporozoite (CS) protein (described in detail by F. Zavala, A. H. Cochrane, E. H. Nardin, R. S. Nussenzweig and V. Nussenzweig in an article in J. Exp. Med. 157:1947 (1983). G. N. Godson, et al., Nature 305:29 (1983) reported that the immunogenicity of the CS protein is restricted almost entirely to a singe epitope which is identically or quasiidentically repeated several times in tandem. See also V. Enea, et al. Proc. Nat'l Acad. Sci. (accepted for publication, 1984).

Circumsporozoite proteins (CS proteins) are members of a family of polypeptides comprising the surface membranes of mosquito salivary gland sporozoites of mammalian malaria parasites of the genus plasmodium. The strong immunogenic properties of sporozoites are associated mainly with the CS protein. This protein, specific for the sporozoite stage, has an immunodominant region of repetitive epitopes. The repeated sequence from N to C terminus of the CS protein for *P. knowlesi* is Gln-Ala-Gln-Gly-Asp-Gly-Ala-Asn-Gly-Gln-Pro-(also designated as QAQGDGANGQP) and the repeated tetrapeptide sequence of the CS protein for *P. falciparum* is Asn-Ala-Asn-Pro-(also designated as NANP). Synthetic peptides consisting of multiples or analogs of the repeated amino acid sequences have been shown to be antigenic and are useful in the development of a malaria vaccine. Unfortunately, however, peptides derived from the immunodominant region of the CS protein display very little homology among themselves and only species-specific antigenicity.

Due to the immunodominance of the repetitive epitopes of the CS protein, it had not heretofore been possible to determine if other segments of the CS protein, which are not within the repetitive domain sequence, can induce antibodies affecting the viability of the parasite. Clearly, immunogenicity itself does not establish the utility of peptides having the sequence of such non-repeating segments as protective antigens against sporozoites, since such segments would need to be on an exposed surface of the CS molecule to allow recognition by antibodies.

OBJECTS OF THE INVENTION

It is an object of this invention to identify regions of the circumsporozoite surface proteins of a member of the genus plasmodium, other than the region containing the repetitive epitope, that contain other, non-repetitive epitopes for such protein.

Another object of this invention is to identify the non-repetitive epitopes of the CS protein, as a prerequisite for the development of an anti-malaria vaccine.

Yet another object of this invention is to identify and synthesize peptides (corresponding to the non-repetitive epitopes of the CS protein) that can elicit formation of antibodies in mammals which can in turn recognize the CS protein, in particular, the CS protein on the surface of sporozoites.

A further object of this invention is to identify and synthesize peptides capable of eliciting formation of antibodies that recognize the CS protein of more than one species of the genus plasmodium.

A further object of this invention is to identify such peptides as a prerequisite for the development of a synthetic malaria vaccine.

A still further object of this invention is to develop an immunogenic element for use in a malaria vaccine for administration to mammals.

SUMMARY OF THE INVENTION

This invention is directed to a peptide comprising an amino acid sequence corresponding to an epitope of a circumsporozoite surface protein of a member of the genus plasmodium, other than the repetitive immunodominant epitope of such protein. The peptide is capable of eliciting formation of antibodies in a host that recognize the circumsporozoite surface protein.

The peptides of the present invention are recognized by, and elicit formation of, antibodies that bind to the CS proteins of the malarial species from which they were derived and also to the CS proteins of other malarial species. This is so because segments of the sequence of CS proteins outside the immunodominant region are extensively homologous. Once one such peptide has been identified, the amino acid (and nucleotide) sequence of other peptides having the same properties can be readily identified by comparing the sequences of CS proteins of different species. These peptides are useful elements in the development of a synthetic malaria vaccine. They can be made by synthetic methods, of they can form part of genetically engineered constructs.

DETAILED DESCRIPTION OF THE INVENTION

Figure 1:
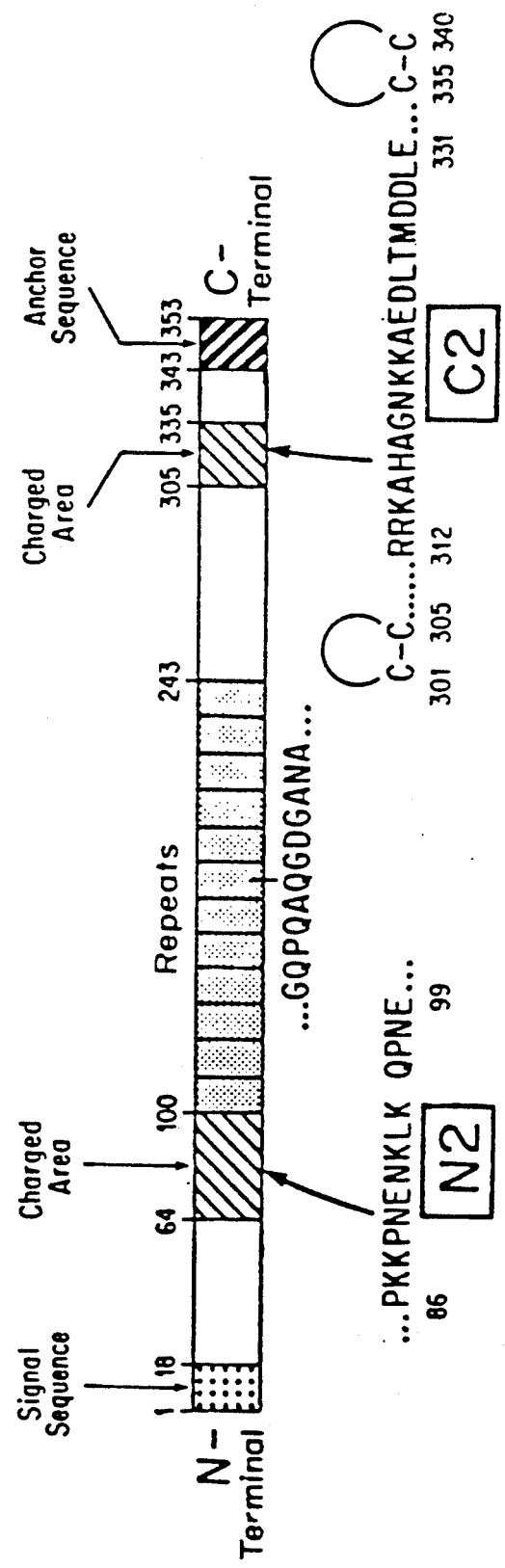
FIG. 1 is a schematic representation of the sequence of the intracellular precursor of *P. knowlesi* CS protein.

The primary structure of the CS protein for *P. knowlesi* and *P. falciparum* was first deduced from the nucleotide sequences of these proteins (Godson, G. N., et al., Nature, 305:29 (Sep. 1983) and Dame, J. B., et al., *Science*, 225:593 (1984)). A schematic representation of the intercellular precursor of *P. knowlesi* CS protein is shown in FIG. 1. Two regions of this protein contain a large number of charged residues (these regions are labeled "charged" in FIG. 1) and may contain an alpha-helical structure. One charged region at the ammo terminal (N-terminus) end of the protein flanks the domain (segment) containing the tandem amino acid repeats. The other charged region, close to the C-terminus, is flanked on each side by a pair of cystein residues.

Peptides having an amino acid sequence corresponding to these charged regions have been synthesized. The polar character of the charged regions indicates that they should be exposed on the surface of the CS molecule. Certain of these peptides are recognized by polyclonal antibodies raised against sporozoites (Vergara, et al., Mol. & Bioch. Parasitol., 1984, in press). Polyclonal antibodies raised against these peptides also recognizes and bind authentic *P. knowlesi* CS protein on the surface of sporozoites, demonstrating the immunogenic properties of such peptides. Antibodies to N2 and C2 peptides (FIG. 1), react on the surface of sporozoites of *P. falciparum, P. vivax, P. malariae, P. brasilianum, P. bergei,* and *P. cynomolgi.*

The data demonstrates that the immunogenic peptides correspond (or are closely related) to the corresponding exposed exterior segments of the CS molecule of most or all species of sporozoites from malaria parasites, and are not excised during intracellular processing of the CS molecule.

Comparison of the N2 and C2 peptides with the corresponding region of *P. falciparum* CS protein, as published in Dame et al, supra, shows a high degree of homology. Significantly, anti-sera raised against these peptides recognize the sporozoites of other species of the plasmodium genus as well.

The partial neutralization by a rabbit antiserum to one of these peptides (N2 in FIG. 1) of the infectivity of sporozoites from an heterologous species, *P. berghei,* demonstrates the presence of a related structure in corresponding regions of CS proteins of this species and that the N2 region is highly conserved in evolution.

Previous evidence shows that antibodies to the repetitive domain of CS protein neutralize infectivity of sporozoites of the species containing that CS protein and suggests that synthetic peptides incorporating the epitope of this repetitive domain could be used in species-specific vaccine preparations. The present invention leads to the conclusion that synthetic polypeptides, or conjugates and/or genetic engineering constructs incorporating the sequence of other peptides, which represent conserved (not species-specific) and exposed regions of the CS molecule, will protect a host against infection by any of several different species of malaria parasites.

EXAMPLE 1: ANTI-SPOROZOITE POLYCLONAL ANTIBODIES

Sporozoites of *P. knowlesi* were obtained from mosquito salivary glands from 10 to 18 days after an infective blood meal, according to the method of Vandenberg, J. P. et al., *Further Studies on the Plasmodium Berghei—Anopheles Stephensi—Rodent System of Mammalian Parasite,* J. Parasitol. 54:1009–1016 (1968). These sporozoites were used to elicit polyclonal antibodies in a rabbit by ten intravenous injections of $10^6$–$10^7$ live sporozoites over a period of three months.

EXAMPLE 2: PEPTIDE SYNTHESIS

Several peptides were chosen for synthesis and immunization. The first was a tetraicosapeptide consisting of a dimer of the repetitive dodecapeptide of the *P. knowlesi* CS protein. This dodecapeptide is designated by the dotted boxes in FIG. 1. The synthesized tetraicosapeptide will be termed "2x repeat". The 2x repeat is a dimer of the amino acid sequence (from N to C terminal) Gln-Ala-Gln-Gly-Asp-Gly-Ala-Asn-Ala-Gly-Gln-Pro.

Two other peptides correspond to segments of the CS protein found in the domains labelled "charged" in FIG. 1. The first one, designated $N_2$, corresponds to amino acids 86–99 in FIG. 1 and has the amino acid sequences Pro-Lys-Lys-Pro Asn-Glu-Asn-Lys-Leu-Lys-Gln-Pro-Asn-Glu.(also designated as PKKPNENKLKQPNE). The second one, designated $C_2$, corresponds to amino acids 312-331 of the CS protein and has the amino acid sequence Arg-Arg-Lys-Ala-His-Ala-Gly-Asn-Lys-Lys-Ala-Glu-Asp-Leu-Thr-Met-Asp-Asp-Leu-Glu.(also designated as RRKAHAGNKKAEDLTMDDLE)

Finally, two additional peptides were synthesized, termed $C_1$ and "charged". The sequence of $C_1$ was taken from the region immediately adjacent to the repeats towards the C terminal. Its overall amino acid composition resembles that of the repeats. The "charged" peptide corresponds to the sequence immediately following $N_2$ towards the N terminal within the charged region. The sequence of $C_1$ is Gly-Lys-Gly-Ala-Gln-Lys-Asn-Gly-Glu-Asn-Gly-Gly-Ala-Pro-Ala-Gly-Gly-Gly-Asn-Arg-Gly-Gln-Arg. (as designated as GKGAQKNGENGGAPAGGGNRGQR). The sequence of "charged" is Lys-Pro-Glu-GLu-Glu-Lys-Glu-Lys-Gly-Lys-Glu-Lys-Lys-Lys-Glu-Lys-Asp-Ala-Gly-Glu-Lys-Pro-Lys-Glu-Gly (also designated as KPEEEKEKGKEKKKEKDAGEKPKEG).

All peptides were synthesized on a Vega Model 250C automated synthesizer (Vega Bio-Chemicals, Inc., Tuscon, Ariz.) controlled by a Motorola computer with a program based on that of Merrified, R. B., Fed. Proc. 21:412 (1962); J. Am. Chem. Soc. 85:2149 (1963).

The synthesis of the dodecapeptide (1x repeat), set forth below, is typical of all peptide synthesis. Three grams of benzhydrylamine resin were suspended and washed three times with methylene chloride ($CH_2Cl_2$), three times with ethanol, and three more times with methylene chloride after placement in the synthesizer.

After a total wash of 2 minutes, the resin was treated with 50% trifluoroacetic acid containing 10% anisole in CH$_2$Cl$_2$ for 30 min., washed ten times with CH$_2$Cl$_2$, and neutralized by washing twice with 10% diisopropylethylamine in methylene chloride. The first BOC amino acid was coupled for one hour to the resin using 3-fold molar excess of dicyclohexyl carbodiimide, in the presence of a 3 molar excess of hydroxybenzotriazole in methylene chloride. Additional aliquots, one of hydroxybenzotriazole and one of diisopropylethylamine, were added at a 3-fold molar excess to BOC-amino acid for an additional hour. The resin was then washed in methylene chloride (3X), absolute ethanol (3X) and methylene chloride (3X), and an aliquot of the mixture was tested using the Kaiser ninhydrin procedure (Kaiser, E. et al., Analyt. Biochem. 34:595 (1970). The resulting peptide was BOC-Gln(NPE)-Ala-Gln(NPE)-Gly-Asp(OBZ)-Gly-Ala-Asn(NPE)-Ala-Gly-Gln(NPE)-Pro-Co-BHA. The protected peptide resin was removed and saved for HF cleavage.

Cleavage was performed in a Peninsula HF apparatus (Peninsula, Laboratory, San Carlos, Calif.) in the presence of anisole (1.2 ml/mg resin) and methylethyl sulfide (1 ml/mg) at 0° C. for one hour, after which the mixture was thoroughly dried under high vacuum. The mixture was then washed with cold anhydrous ether, extracted with alternate washes of water and glacial acetic acid and lyophilized.

The crude peptides (200 mg aliquots) were desalted by gel filtration on a Sephadex G-25 column )120×2.0 cm) that had been equilibrated with 0.1 NH$_4$HCO$_3$, pH 8.0. The column effluent was monitored by UV absorbance at 254 and 206 nm with an LKB UV-Cord III monitor. The collected peptides were then characterized.

EXAMPLE 3: PURIFICATION OF ANTIBODIES CAPABLE OF REACTING WITH SPECIFIC SYNTHETIC PEPTIDES

Polyclonal antibodies recognizing the peptides were isolated from the anti-sporozoite rabbit antisera prepared in Example 1. The peptides were coupled to activated Sepharose-4B beads (Pharmacia Fine Chemical Company, Piscatway, N.J.) according to the manufacturer's instructions. The beads were subsequently treated for one hour with 0.005 M glutaraldehyde in 0.25 M NaHCO$_3$, pH 8.8. The washed beads were incubated with 1 M ethanolamine, 9.0, for one hour, washed again in and resuspended in phosphate-buffered saline (PBS), pH 7.4.

To remove any non-specific binding substances, the anti-knowlesi antiserum was first adsorbed with beads conjugated to a non-relevant peptide. For example, to purify anti-C$_2$ antibodies, a sample of antiserum was sequentially adsorbed with N2-bearing beads, then with beads bearing peptides corresponding to other segments of the charged regions, and, finally with repeat-bearing beads. The supernatant resulting from the last adsorption was then incubated for several hours at room temperature with beads containing the peptide of interest. After washing repeatedly with PBS, the bound antibodies were eluted from the beads by treatment with 3 M potassium thiocyanate. The eluate was immediately filtered through a small Sephadex G-25 column to remove small molecules. These purified antibodies were used to assay the synthetic peptides.

EXAMPLE 4: IMMUNORADIOMETRIC ASSAY

Synthetic peptides N$_2$, C$_2$ "charged" (corresponding to amino acids 99-86 of the P. knowlesi CS protein), C1 (corresponding to amino acids 267-245) and "2x repeat" were prepared in accordance with the method of Example 2. The peptides were separately diluted to 20 micrograms/ml in 0.1 M NaHCO$_3$, pH 9.6. Fifty microliters of the solution were delivered to wells of polyvinyl chloride flexible microtiter plates (Dynatech Laboratories, Inc., Alexandria, Va.). After incubation overnight at 4° C., the wells were washed three times with buffer containing Tween 20 (Biorad Laboratories, Richmond, Calif.), treated with 1% bovine serum albumin (BSA) in PBS for two hours at 4° C. and washed. Subsequently, 25 microliters of serial dilutions of the appropriate rabbit anti-sporozoite antiserum (from Example 3), were delivered to the wells, and the plate was incubated for 2 hours at 4° C. After washing, the wells were incubated for 2 hours with 5×10$^4$ cpm in 30 microliters of $^{125}$I-labelled affinity-purified goat anti-rabbit IgG diluted in PBS containing 1% BSA. The wells were washed, cut and counted. As negative controls, peptide-coated wells were incubated with normal rabbit serum and treated as above. The results show that the rabbit anti-sporozoite antiserum contained antibodies directed against the 2x repeat and the N2 and C2 peptides (the counts obtained in control wells incubated with dilutions of normal rabbit serum are subtracted from the counts obtained in experimental wells). The results show that the antiserum recognizes four peptides, N2, C2, "charged" and "2X repeat," but not C1.

The specificity of the reaction was evaluated by inhibition assays. A constant dilution of the anti-sporozoite antiserum was incubated with serial dilutions of homologous peptides prior to delivering to the wells of the microtiter plates and this was followed, as above, by treatment of the wells with $^{125}$I-labeled goat anti-rabbit IgG. The results show that the rabbit anti-sporozoite antiserum specifically recognizes the N2, "charged", "2x repeat" and C2 peptides. Most of the reactivity of this antiserum was directed against the repetitive epitope and the C2 peptides, while titers of antibodies against the N2 peptide were rather low. The binding was specific since it was inhibited only by the homologous peptides.

EXAMPLE 5: IMMUNOBLOTTING

To rule out the possibility that the recognition of the peptides by anti-sporozoite antibodies could be the product of spurious cross reactions with irrelevant antigens present in the sporozoite preparation, the affinity-purified anti-C$_2$ anti-peptide antibodies were assayed by Western blotting against sporozoite extracts. The results show that these antibodies recognize both the intracellular precursor and the membrane-associated CS protein. Immunoradiometric assays of anti-C2 against the repeat peptide were negative, indicating that contaminant antibodies were not present.

Western blotting was performed as follows: Sporozoite extracts (10$^5$/ml.) were subjected to electrophoresis in a 10% sodium dodecylsulfate polyacrylamide gel. The separated proteins were electrophoretically transferred to nitrocellulose sheets (as disclosed by Towbin, H., et al., Electrophoretic Transfer of Proteins From Polyacrylamide Gels to Nitrocellulose Sheets: Procedure and Some Applications, Proc. Natl. Acad. Sci. (USA) 76:4350-4354 (1979)). The nitrocellulose paper was saturated with PBS containing 5% BSA and normal goat serum for one hour at 37° C. The various lanes were cut and each lane was incubated with a different affinity-purified anti-peptide antibody. Antibodies against "2x repeat", "charged", and $C_2$ peptides were used. Antiserum against whole sporozoite was used as a control. After extensive washing with PBS containing 1% BSA, the strips were incubated for 2 hours at room temperature with affinity-purified $^{125}$I-labelled goat anti-rabbit IgG. The strips were washed, dried, and exposed to autoradiography. Two specific bands were obtained in all cases, one corresponding to a molecular weight of 52,000 daltons (intracellular precursor of *P. knowlesi* CS protein) and one corresponding to a molecular weight of 42,000 daltons (*P. knowlesi* CS protein itself). Anti-repeat activity was only detected in the wells incubated with dilutions of the antisporozoite antiserum.

EXAMPLE 6: ANTIBODY ELICITATION BY THE SYNTHETIC PEPTIDES

The synthetic peptides, 2x repeat, N2, and C2, were conjugated to keyhole limpet hemocynin using carbodiimide, according to the method of Likhite, V. et al., in Methods in Immunology and Immunochemistry. Curtis C. A. and Chase, W. A., (Eds.), Academic Press, N.Y., 1967, pp. 150–157. The conjugates were emulsified in complete Freund's adjuvant and injected into rabbits and mice. Conjugate was injected into the footpad of rabbits (500 micrograms) and mice (100 micrograms). The animals were bled 6 weeks after immunization. The antisera were assayed against glutaraldehyde-fixed sporozoites of every species of malaria parasites by indirect immunofluorescence, as disclosed by Nardin, E. H., et al. R. Bull. WHO 57(Suppl.): 211–217 (1979). While the antisera to the repeats were strictly species-specific, i.e. recognized only *P. knowlesi*, the antisera to N2 and C2 also reacted with *P. berghei, P. cynomolgi, P. falciparum, P. vivax, P. malariae,* and *P. brisilianum*. When incubated with *P. berghei* sporozoites, both anti-N2 and anti-C2 gave CSP reactions. This means that that they induced formation of a prominent, tail-like, precipitate at the posterior end of the parasite, as reported by Vandenberg, J., et al., Mil. Med. 154(Supp.): 1183–1190 (1969). All reactions were specific since they were inhibited by the homologous but not by the heterologous peptide at concentrations of 50 micrograms per microliter in the incubation medium. None of the antisera reacted with sporozoites of *P. gallinaceum*.

The above results indicate that C2 and N2 are exposed on the exterior of the CS molecule and that they are accessible to interaction with antibodies. Moreover, the reactivity of anti-N2 and anti-C2 with sporozoites strongly suggests that the corresponding peptides are represented on the parasite surface, and are not removed during intracellular processing. This was confirmed by immunoblotting with extracts of *P. berghei* and *P. falciparum* sporozoites.

EXAMPLE 7: IMMUNOBLOTTING OF *P. BEGHEI* SPOROZOITES

*P. berghei* ($10^5$ sporozoites per lane) were subjected to electrophoresis on SDS-PAGE (10%) and the proteins were transferred to nitrocellulose. After saturation with 5% BSA, and incubation with 5% goat serum, the cellulose strips, were incubated with monoclonal (anti-*P. berghei* antibodies 3D11, anti-C2, or anti-N2, washed and reincubated with a second radiolabeled antibody (affinity purified goat anti-rabbit or anti-mouse immunoglobulin). The washed strips were then subjected to autoradiography. In *P. berghei* extracts, two specific polypeptides of Mr 52,000 *and* 44,000 were detected by anti-N2 and anti-C2. The 44,000 Mr protein represents the processed form of the 52,000 polypeptide and is found on the surface membrane of the *P. berghei* parasite. We conclude that the surface polypeptide must contain structures, most likely at the C-terminal and N-terminal ends of the molecule, closely resembling C2 and N2, respectively.

Figure 2:
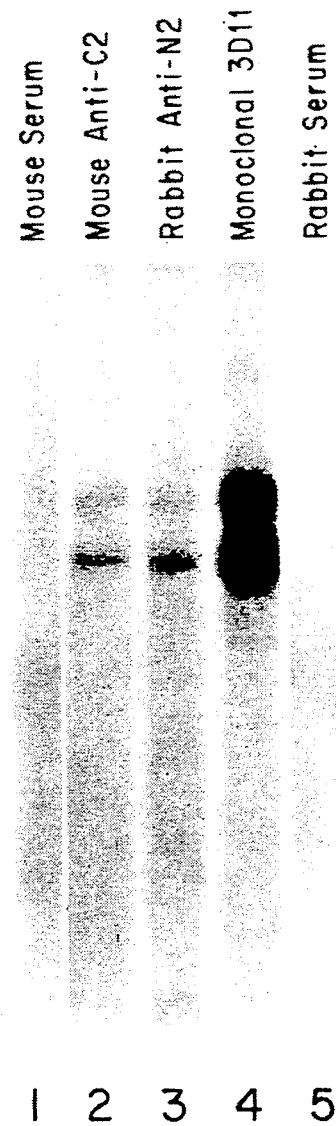
FIG. 2 is an autoradiograph of Western blotting (immunoblotting) of antibodies to synthetic peptides N2 and C2 of the present invention with *P. berghei* sporozoite extracts.

The results of this immunoblotting experiment are shown in FIG. 2. Lanes 1 and 5 are the controls, containing mouse and rabbit serum, receptively. Lane 2 contains mouse anti-$C_2$, lane 3 contains rabbit anti-$N_2$ and lane 4 contains monoclonal anti-CS for *P. berghei*. Western blotting with *P. falciparum* using the same methodology was also positive with anti-C2 and anti-N2.

EXAMPLE 8: PARTIAL NEUTRALIZATION OF *P. BERGHEI* SPOROZOITES BY RABBIT ANTI-N2 (*P. KNOWLESI*)

Antiserum (0.2 ml), or normal rabbit serum as a control, was incubated for 45 min at room temperature with 0.5 ml of medium 199 (Gibroc, Grand Island, N.Y.) containing $3 \times 10^4$ sporozoites obtained by dissection of salivary glands of Anopheles mosquitoes. After incubation, 1 ml of medium was added and 0.2 ml ($5 \times 10^3$ sporozoites) were injected intravenously into five A/J mice, which were then examined daily for presence of the blood stage of the parasite. In four separate experiments, there was evidence of partial neutralization of the parasites by anti-$N_2$.

Some of the mice inoculated with parasites treated with anti-$N_2$ did not become patent. In all experimental groups the prepatent periods were longer than those of the controls. The results are shown in the following Table 1:

TABLE I

| No. of Mice Infected/No. of Mice Injected (Day of Patency ± SD) After Incubation of Sporozoites with: | | |
|---|---|---|
| Experiment No. | Anti-$N_2$ | Normal Serum Control |
| 1 | 0/5 | 5/5 (5.6 ± 0.4) |
| 2 | 4/5 (6.4 ± 0.4) | 5/5 (4.8 ± 0.4) |
| 3 | 5/5 (5.4 ± 0.4) | 5/5 (4.0) |
| 4 | 5/5 (5.6 ± 0.7) | 5/5 (4.4 ± 0.7) |

This increase in prepatent period is highly significant, considering that the dose response curve relating the dose of sporozoites injected to the first day of patency is quite flat, as reported by Schmidt, N. H., et al., Am. J. Trop. Med. Hyg. 31(Suppl):612–645 (1982).

In two other similar experiments, rabbit antiserum to C2, which had given a very strong CSP reaction (between mature infective sporozoites and antiserum) with *P. berghei* sporozoites, had no discernible effect on their infectivity for mice.

EXAMPLE 9: ALIGNMENT OF HOMOLOGOUS AREAS OF CS PROTEINS OF DIFFERENT SPOROZOITES SPECIES

The computer program ALIGN, reported by Dayhoff, M. O., et al. in Methods and Enzymology (Editors: Hirs, C. H. W. and Timasheff, S. N.) 91:524–545 (Academic Press, N.Y., N.Y. 1983) was used to evaluate the homology between the areas containing the repeats of 3 circumsporozoite proteins: *P. knowlesi, P. falciparum* and *P. cynomolgi.*

The repeats of these three proteins are quite distinct (QAQGDGANAGQP for *P. knowlesi,* PNAN for *P. falciparum* and DGAAAAGGGGN for *P. cynomolgi*). The key for this notation is: A=alanine; R=arginine; D=aspartic acid; Q=glutamine; N=asparagine; E=-glutamic acid; G=glycine; I=isoleucine; L=leucine; P=proline; S=serine; T=threonine; Y=tyrosene; V=valine; K=lysine; C=cysteine; M=methonine;; H=histidine.

The scores were significant only for the comparison between *P. knowlesi* and *P. falciparum* repeats (4.41 SD, where a score of 3.0 indicates a probable relatedness). This accounts for the fact that certain monoclonal antibodies to the *P. knowlesi* repeats cross-react weakly with *P. falciparum*, as reported i Cochrane, et al., Proc. Natl. Acad. Sci. (USA) 79:5651 (1982).

By contrast, when the ALIGN program was used to analyze the three sequences excluding the region of the repeats, the scores were all highly significant, to wit, 23.37 S.D., 24.57 S.D. and 16.28 S.D. for comparisons between *P. knowlesi* and *P. falciparum, P. cynomolgi* and *P. knowlesi,* and *P. cynomolgi* and *P. falciparum,* respectively.

Figure 3:
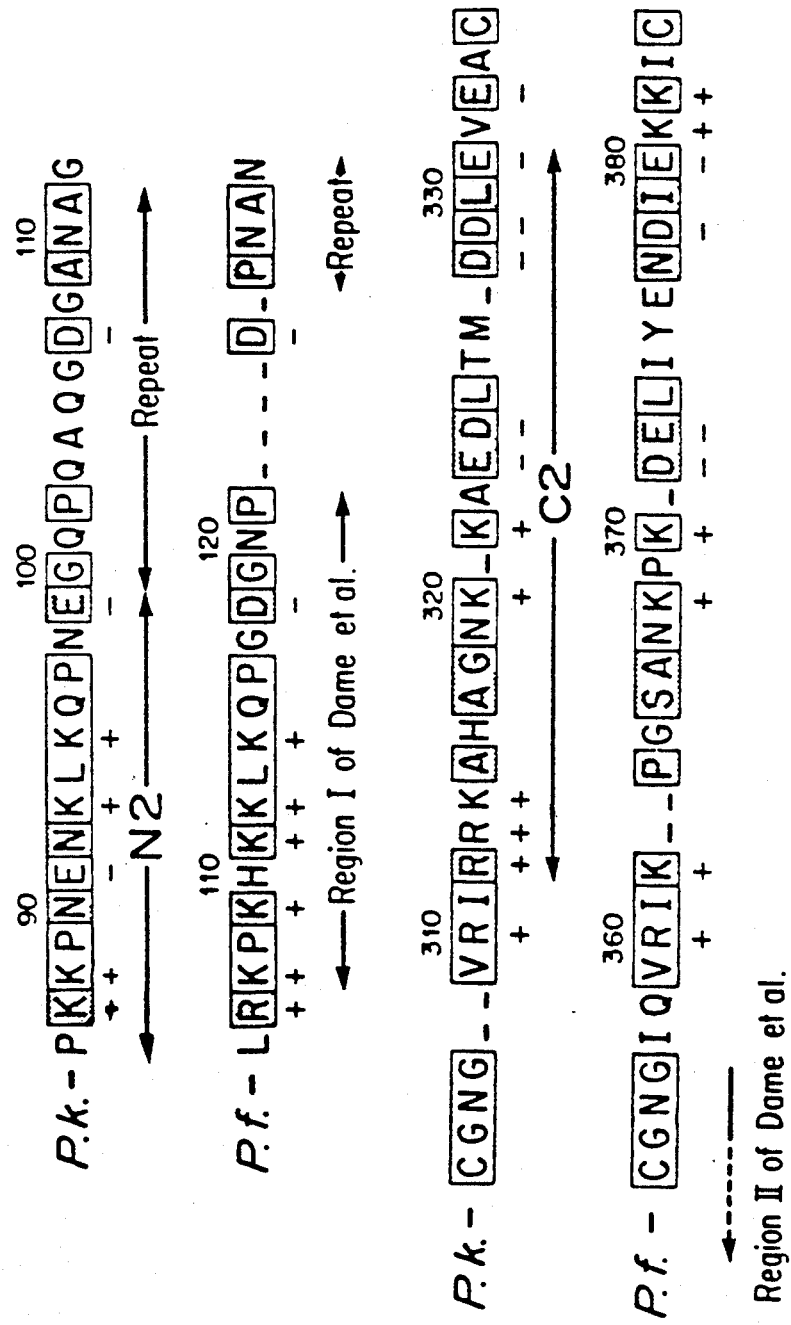
FIG. 3 is a schematic representation of segments of the *P. knowlesi* and *P. falciparum* CS protein outside the immunodominant epitope of these proteins. These segments have been aligned to achieve the highest degree of homology.

A particularly high degree of homology, most likely sufficient to preserve the tertiary structure and the functional properties of these domains, was observed between $N_2$ and $C_2$ of *P. knowlesi* with peptides in the corresponding charged areas of *P. falciparum* (See FIG. 3). These two sequences were aligned by visual inspection to achieve the maximum degree of homology. The homologous areas are indicated by white boxes in FIG. 3. The shaded boxes show residues which are known to be frequently interchanged by single-base substitutions among homologous proteins, as established by McLachlan, A. D., J. Mol. Biol. 61:409–424 (1971).

The extensive homology of these regions, which extends to the initial amino acids of the repeat segment of *P. knowlesi*, is evidence of a high degree of inter-species conservation of the structure of this region of the CS protein. This suggests that the N-terminal end of these CS molecules may be involved in an important sporozoite function.

This alignment of the homologous regions of CS proteins of different species can be used to identify homologous peptides in CS proteins of different species. Thus, the region of the *P. falciparum* CS protein corresponding to $N_2$ of *P. knowlesi* will have the amino acid sequence: Arg-Lys-Pro-Lys-His-Lys-Lys-Leu-Lys-Gln-Pro-Gly-Asp.

Similarly, the region of the *P. falciparum* CS protein corresponding to $C_2$ will have the structure: Lys-Pro-Gly-Ser-Ala-Asn-Lys-Pro-Lys-Asp-Glu-Leu-Ile-Tyr-Glu-Asn-Asp-Ile-Glu.

Once the amino acid sequences of such peptides are known, the corresponding nucleotide sequences can be derived. DNA fragments comprising these nucleotide sequences may be used in genetic engineering constructs in conjunction with DNA fragments corresponding to their repeats, to prepare genetically engineered antigens capable of eliciting antibodies in a host with increased neutralization activity against sporozoites. This activity crosses species lines and is therefore of considerable importance as an element in the creation of a vaccine to protect mammals against malaria.

What is claimed is:

1. A peptide antigen comprising an amino acid sequence of a non-repetitive epitope of the circumsporozoite protein of a sporozoite of the genus splasmodium, said peptide having the property of eliciting formation of antibodies that bind to said non-repetitive epitope on the sporozoite surface, said peptide being synthetic, purified, and substantially shorter in length than said protein.

2. The peptide antigen of claim 1, wherein said peptide has been synthesized by recombinant techniques.

* * * * *